(12) United States Patent
Ibanez

(10) Patent No.: US 11,511,123 B2
(45) Date of Patent: Nov. 29, 2022

(54) IMPLANTABLE MEDICAL DEVICE AND METHOD OF PROVIDING WIRE CONNECTIONS FOR IT

(71) Applicant: Oticon Medical A/S, Smørum (DK)

(72) Inventor: Hervé Ibanez, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 500 days.

(21) Appl. No.: 16/654,598

(22) Filed: Oct. 16, 2019

(65) Prior Publication Data
US 2020/0121934 A1   Apr. 23, 2020

(30) Foreign Application Priority Data
Oct. 17, 2018   (EP) .................................... 18200910

(51) Int. Cl.
*A61N 1/375*   (2006.01)
*H01R 13/52*   (2006.01)
*H01R 43/00*   (2006.01)

(52) U.S. Cl.
CPC ....... *A61N 1/3754* (2013.01); *H01R 13/5202* (2013.01); *H01R 13/5224* (2013.01); *H01R 43/005* (2013.01); *A61N 1/37512* (2017.08); *A61N 1/37514* (2017.08)

(58) Field of Classification Search
CPC .............. A61N 1/3754; A61N 1/37512; A61N 1/37514; H01R 13/5202; H01R 13/5224; H01R 43/005
See application file for complete search history.

(56) References Cited

U.S. PATENT DOCUMENTS

| | | | |
|---|---|---|---|
| 4,207,441 A | 6/1980 | Ricard et al. | |
| 4,532,930 A | 8/1985 | Crosby et al. | |
| 4,970,351 A | 11/1990 | Kirlin | |
| 5,967,194 A | 10/1999 | Martin | |
| 2002/0019669 A1* | 2/2002 | Berrang | A61N 1/36038 607/137 |
| 2002/0055732 A1 | 5/2002 | Wilson | |
| 2008/0092974 A1 | 4/2008 | Gleeson | |
| 2010/0241206 A1 | 9/2010 | Truex et al. | |
| 2015/0165192 A1* | 6/2015 | Walling | A61N 1/375 607/137 |
| 2016/0010422 A1 | 1/2016 | Goodman | |
| 2016/0045723 A1* | 2/2016 | Bornzin | A61N 1/37514 607/45 |

FOREIGN PATENT DOCUMENTS

| | | |
|---|---|---|
| EP | 3 111 993 A1 | 1/2017 |
| WO | WO 2004/026199 A2 | 4/2004 |
| WO | WO 2004/026199 A3 | 4/2004 |

* cited by examiner

*Primary Examiner* — Lindsey G Wehrheim
(74) *Attorney, Agent, or Firm* — Birch, Stewart, Kolasch & Birch, LLP

(57) ABSTRACT

An implantable medical device comprising a sealed flat housing enclosing an electronic circuitry; a plurality of feedthrough conductors, each feedthrough conductor comprising a proximal end part connected to the enclosed electronic circuitry and a distal end part extending from a side surface of the housing and cumulated on said side surface; a tubing that houses a plurality of wires connected to said feedthrough conductors and that is arranged on the housing; and a longitudinal slit through the wall of the tubing through which the wires extend out of the tubing.

15 Claims, 2 Drawing Sheets

IMPLANTABLE MEDICAL DEVICE AND METHOD OF PROVIDING WIRE CONNECTIONS FOR IT

FIELD

The present disclosure relates to implantable medical devices. More particularly, the disclosure relates to implantable devices with electrical contacts where electrical wires are attached like cochlear implants, heart pacemakers, or brain stimulating devices. The electrical wires are connected to an electrode that serves for sensing and/or stimulating a bodily part such as a cochlea, a heart muscle, or a particular area of the brain.

BACKGROUND

Implanted medical devices utilize hermetically sealed housings to isolate the device from the body environment. Such devices require that electrical signals are passed from within the housing to external connectors or vice-versa while maintaining hermetical tightness of the housing. Depending upon the configuration of the implantable device, there may be multiple electrical paths required between an electronic circuitry enclosed within the housing and the external electrical contacts. These paths are usually electrically and mechanically integrated with the device in order to provide a safe, long-term arrangement that does not compromise hermetic housing.

Many devices use feedthrough conductors to transfer electrical signals between the inside of the hermetically sealed housing and the outside of said housing. The distal end parts of the feedthrough conductors are available externally to the housing and serve as contact portion for the electrodes that are implanted in a tissue of a bodily part.

Conventionally, the electrical connection between the feedthrough conductor and the electrode is made by positioning a plurality of connectors over a non-conductive unit, thereby connecting one end of each connector to a corresponding feedthrough conductor. The other end of each connector is guided towards the outer periphery of the housing.

At the outer peripheral surface of the housing, each other end of the connector is connected to a respective wire. While maintained electrically insulated, the wires are routed together so as to run jointly through a wire entry/exit port and further away from the housing towards the electrode.

During the manufacturing of the device, and later, during the implantation, an impact may be applied to the device. As the electrical connections between the connectors and the wires are in an exposed position, at a side of the housing, the connections are sensible to any external impact. Such an impact may involve a pull-out force applied to the wires in a direction away from the housing or a bending stress. The effect may be that connections between the connectors and the wires are broken, which leads to low reliability and involves additional rework.

To prevent the above described effects, a method of providing additional wire length is known from the prior art. According to the method, the wires are longer than actually needed for making the connections, thereby providing an extra length for compensating any wire extension caused by external deformation. The additional wire lengths are provided in a non-conductive unit and arranged in wire loops, for example.

The method of providing additional wire length requires a series of complicated manufacturing operations. Not only have the wires to be arranged in loops, but also electrical insulation of the wires from each other must be ensured. The manufacturing operations have to be carried out by specialized operators and are time consuming.

Therefore, there is a need to provide a solution that addresses at least some of the above-mentioned problems.

SUMMARY

According to an aspect, an implantable medical device is disclosed. The device includes a sealed flat housing that encloses an electronic circuitry and a plurality of feedthrough conductors. Each feedthrough conductor comprises a proximal end part connected to the enclosed electronic circuitry and a distal end part extending from the side surface of the housing and cumulated on said side surface. The device further comprises a tubing that houses a plurality of wires connected to said feedthrough conductors and arranged on the housing. There is a longitudinal slit through the wall of the tubing through which the wires extend out of the tubing.

The feedthrough conductors extend from the side surface of the housing to ensure a reliable wire connection. However, the feedthrough conductors could also be flat so as to be flush with the side surface of the housing.

The feedthrough conductors are cumulated on a side surface of the housing. This includes that the plurality of feedthrough conductors may be arranged in an array or distributed randomly on said side surface. The two-dimensional arrangement on the side surface allows reasonable spacing between the each feedthrough conductor and wire and benefits establishing reliable connections (e.g. weld connections), even though the feedthrough conductors are closely concentrated in a small area.

A tubing is used to house the plurality of wires. The tubing provides protection for the wires against external impacts. During manufacturing, the tubing allows guiding the wires commonly and facilitates the assembly step of connecting the wires to the feedthrough conductors.

The tubing is provided with a longitudinal slit that allows to pull out wires from the inside to the outside of the tubing or to thread wires from the outside to the inside of the tubing. Due to the longitudinal slit, it is easier to pass the wires through the wall of the tubing than to make only a small cut for each wire and to thread each wire through the individual small cut. With the longitudinal slit, a wire can be started passing through the wall of the tubing at a longitudinal end of the tubing where it is easier to pass it through and then be pulled along the longitudinal slit until it is extending from the tubing at a predetermined position. The predetermined position is defined by the perfect location of perpendicular slits which allow an easy connection between the wire selected and the right feedthrough conductor.

In an embodiment, the tubing has at least one additional slit substantially perpendicular to the longitudinal slit. The perpendicular slit serves for fixing the longitudinal position where a wire is extending out of the tubing. Thereby, it is ensured that the wire exit position is not changed, in case an axial stress, such as a pull-out force, is applied to the wire during the manufacturing or during use.

In an embodiment, at least two wires extend out of the tubing at different longitudinal positions of the tubing. This allows each wire to exit the tubing at a position close to the feedthrough conductor to which it is connected. Thereby, the unprotected wire length outside the tubing is reduced for each wire. Further, as the wires extend out of the tubing at different longitudinal positions of the tubing, they are provided with a clearance between them. This clearance reduces the risk of any short circuit between the wires in their unprotected area outside the tubing.

In an embodiment, a wire length from a wire exit position at the tubing to a fixed wire end is the same for the at least two wires. This enables the manufacturer to cut the two or more wires in one step and in one fixture, instead of measuring each wire length separately and differently and cutting each of them accordingly.

In an embodiment, the wire extension directions from the wire exit positions at the tubing to the fixed wire ends are different for the at least two wires. Such a configuration is used if the feedthrough conductors are cumulated in a relatively small area in order to have a maximized clearance between the wires. This facilitates the assembly and ensures reliable electrical connections due to a reduced risk of short circuits in the cumulated area.

In an embodiment, the implantable medical device further comprises a wire guide arranged on said side surface of the housing. In the wire guide, a plurality of guide grooves are formed for guiding the wires. This ensures that the wires are safely guided from their respective exit position at the tubing to the connection position at the feedthrough conductor. Such a wire guide assists the operator in arranging the wires during the manufacturing and thereby increases the reliability of this process.

In an embodiment, the tubing runs along the outer periphery of the wire guide. For example, the tubing may be arranged to run around an outline of the wire guide so as to form a loop around the wire guide. However, the tubing can also be arranged along a part of the periphery of the wire guide. With the tubing running along the outer periphery of the wire guide, the contact surface between the both members is increased. In particular, a tubing that runs around curves and corners of the wire guide has an increased wrap angle around the wire guide. This has the effect that the friction between the tubing and the wire guide is increased and thereby the mechanical stability of both parts relative to each other is increased. For example, if a pull-out force is applied to the tubing, the resistance against displacement of the tubing relative to the wire guide is increased without requiring additional fixing members and space. Thereby, the reliability of the electrical connections is increased, as the wires or the connections of the wires are less likely to break in case of an external mechanical impact.

In an embodiment, the wire guide has a hole through which the distal end part of the feedthrough conductor is exposed. Depending on the arrangement of the feedthrough conductors, each feedthrough conductor can be exposed through a separate hole or more than one feedthrough conductors can be exposed through a common hole. This enables that the areas around the feedthrough conductors, such as a housing surface, are covered by the wire guide and, therefore, protected. Consequently, it is facilitated to connect only the distal end part of the feedthrough conductor, which is the relevant part for making an electrical connection, with the wire. A risk for creating a short circuit between the wire and a part other than the feedthrough conductor is reduced and leads to a better reliability. In particular, in case the connection between the wire and the feedthrough conductor is made by material addition, such as welding or soldering, it is prevented that the added material spreads unintentionally.

In an embodiment, a first end of each guide groove communicates with an outer periphery of the wire guide and a second end of each guide groove communicates with the feedthrough conductor. Thereby, the part of the wire outside the tubing is housed in the guide groove along its whole length across the wire guide. This ensures protection of the wire. Further, by guiding each wire in a separate groove towards the feedthrough conductor, the risk of erroneously connecting a wire to another feedthrough conductor than the predetermined one is reduced.

In an embodiment, a plurality of connectors configured to provide connections for the plurality of wires are used. Each connector comprises a first end section adapted to be connected with a feedthrough conductor and a second end section adapted to be connected with a wire. The connector is used as a terminal to facilitate the connection between the wire and the feedthrough conductor, for example in a soldering or welding process.

In an embodiment, the wire guide is made from an electrically insulating material. This ensures that the wires are housed electrically insulated from each other and from the housing. A risk of short circuit is thereby reduced.

According to the embodiment, a method of providing connections for a plurality of wires in an implantable medical device is disclosed. The method comprises preparing a sealed flat housing enclosing an electronic circuitry, wherein said housing has a plurality of feedthrough conductors. Each feedthrough conductor comprises a proximal end part connected to the enclosed electronic circuitry and a distal end part extending from the side surface of the housing and cumulated on said side surface. The method involves taking a tubing and cutting a longitudinal slit through the wall of a tubing and passing wires through the slit. The tubing is arranged on said housing and each wire is connected to a corresponding feedthrough conductor.

At the step of passing wires through the wall of the tubing, it is possible either to pull out wires from inside the tubing through the slit or to introduce the plurality of wires into an empty tubing through the slit. In both cases, the wires can be passed through the wall of the tubing easily in comparison to threading each wire through only a small cut or hole in the tubing. This allows starting the passing through step at a longitudinal end of the tubing, where the longitudinal slit opens up to the hole in the axial end surface of the tubing. At the intersection of the longitudinal slit and the hole, it is much easier to pass the wires through the wall, because it is not necessary to start with a free wire end. Any part of the wire can be used to start the passing through step and preferably, the wire is passed through the slit laterally. Having the wires passed through the wall, they are pulled along the longitudinal slit with one end of the wire, while the other end inside the tubing is fixed relative to the tubing. The pulling is continued until the wire is extending from the tubing at a predetermined position.

The tubing is arranged on the housing so as to allow each wire to be connected with a feedthrough conductor.

Preferably, at least one slit substantially perpendicular to the longitudinal slit is provided at the tubing. This simplifies the passing through step for the operator. Further, the perpendicular slit serves for fixing the longitudinal position of a wire exit through the wall of the tubing. In case a wire exits the tubing through the longitudinal slit, the exit position may be influenced if the wire and the tubing are moved relative to each other in an axial direction, such as pulling one end of the wire. However, a slit substantially perpendicular to the longitudinal slit allows a wire only to move along the slit in a circumferential direction of the tubing and thereby restricts any displacement of the longitudinal wire exit position. Consequently, it is ensured that the wire exit position is not changed, in case an axial stress, such as a pull-out force, is applied to the wire during the manufacturing or during use.

Preferably, a wire length from a wire exit position at the tubing to a fixed wire end is the same for the at least two wires. This enables the operator during manufacturing to cut the two or more wires in one step and in one fixture. In particular, all wires can have the same length from a wire exit position at the tubing to a fixed wire end.

In particular, a wire guide, in which a plurality of guide grooves for guiding the wires are formed, is arranged on a side surface of the housing. This facilitates the step of placing the wires in the guide grooves.

In particular, the guide grooves have the same length as the wires that are to be placed therein.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other embodiments. These and other embodiments, features and/or technical effect will be apparent from and elucidated with reference to the illustrations described hereinafter in which:

DETAILED DESCRIPTION

Figure 1:
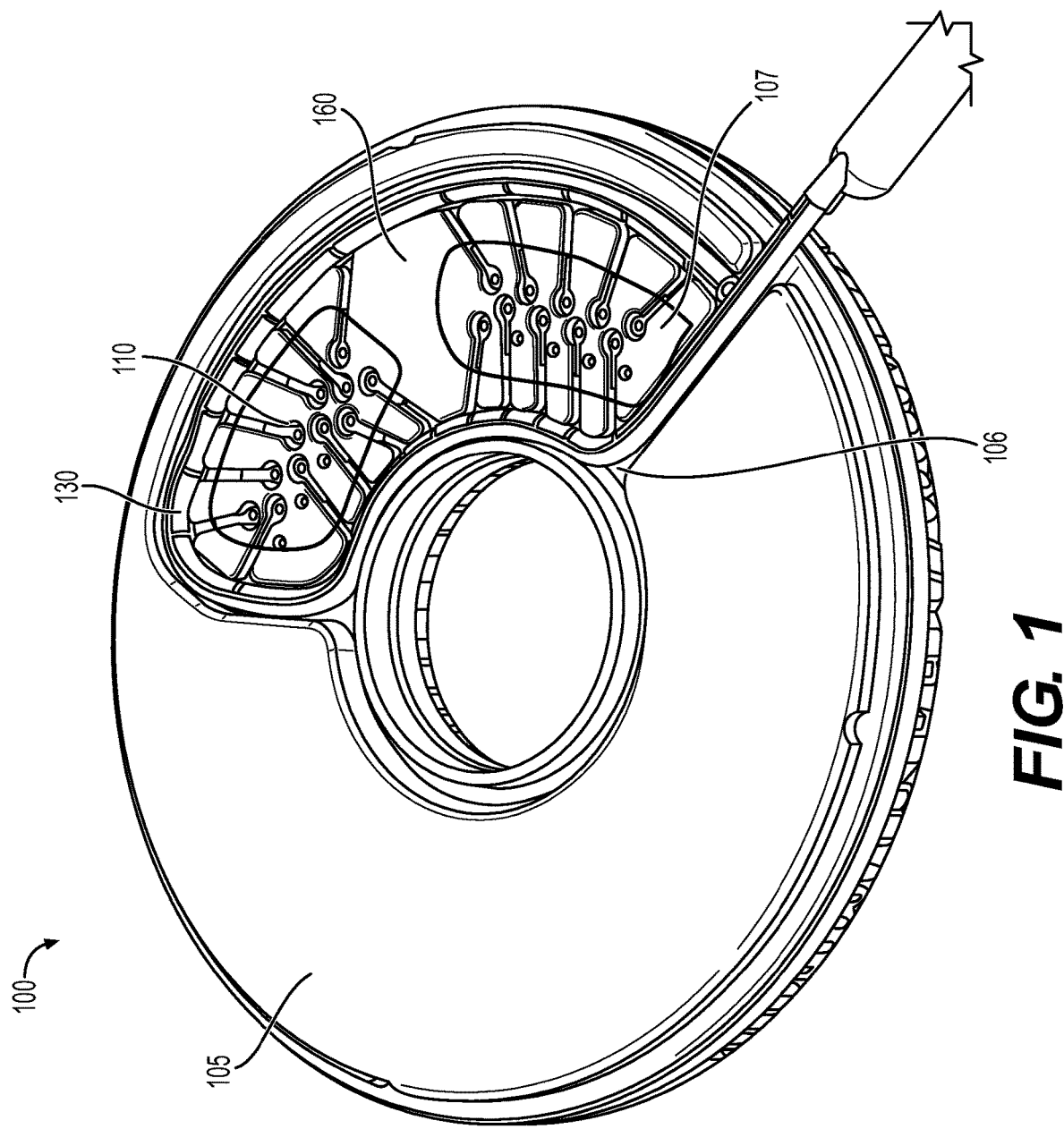
FIG. 1 illustrates an implantable medical device according to an embodiment.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

It is intended that the structural features of the devices described above, either in the detailed description and/or in the claims, may be combined with steps of the method, when appropriately substituted by a corresponding process.

FIG. 1 illustrates an implantable medical device 100 according to an embodiment. The implantable medical device 100 includes a sealed housing 105 that encloses an electronic circuitry. The housing 105 is flat and has a circular outline in a plan view. When viewed in said plan view, the housing 105 further has a circular through hole arranged concentrical to the circular outline of the housing 105. Thereby, two side surfaces with the shape of a circular ring are formed on each side of the housing 105.

A recess area 106 is formed on one side surface of the housing 105. In the recess area 106 two protrusion areas 107 are protruding and a plurality of feedthrough conductors 110 are extending from each protrusion area 107. Each protrusion area 107 has a substantially rectangular shape with rounded corners.

Figure 2:
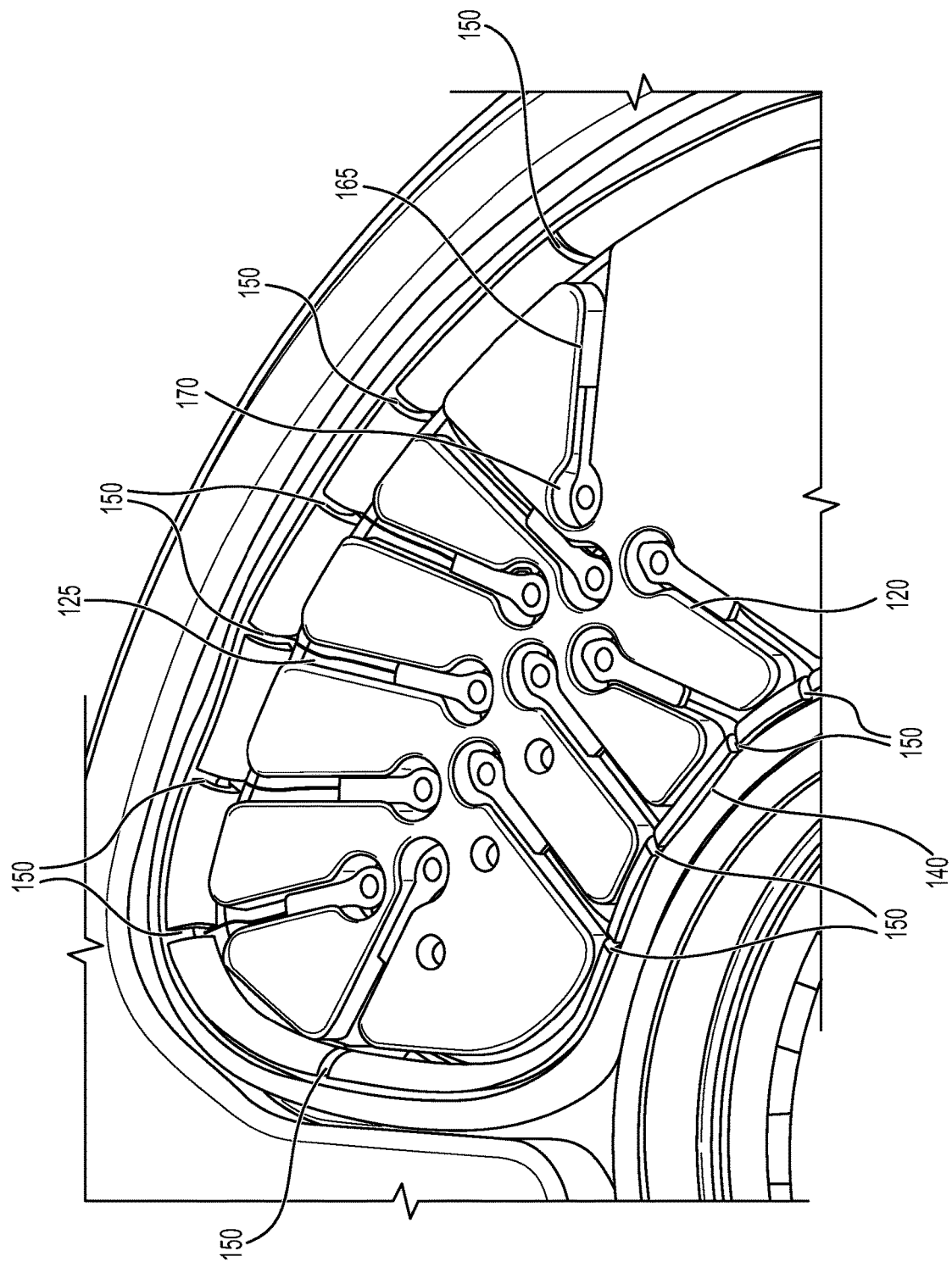
FIG. 2 illustrates an enlarged view of the side surface of the housing where the feedthrough conductors are cumulated.

The plurality of feedthrough conductors 110 are cumulated on each protrusion area 107. FIG. 2 illustrates in an enlarged scale that the feedthrough conductors 110 are arranged in three rows, wherein the two outer rows each comprise five feedthrough conductors 110 equally spaced apart from each other. The middle row comprises four feedthrough conductors 110 equally spaced apart from each other, which are jointly shifted in a direction in which the row extends. Thereby, the clearance between the feedthrough conductors 110 of the middle row and the feedthrough conductors 110 of the two outer rows is enlarged.

Each feedthrough conductor 110 of the plurality of feedthrough conductors 110 comprises a proximal end part (not shown) connected to the enclosed electronic circuitry and a distal end part available externally to the housing 105. Each distal end part has a cylindrical shape and extends from the protrusion area 107.

The implantable medical device 100 further comprises a tubing 130. The tubing 130 has a tubular shape and is made of a flexible material so that it can be bent along its longitudinal axis.

One end of the tubing 130 extends from the housing 105 towards the electrodes of the implantable medical device 100 in a radial direction of the circular outline of the housing 105.

The other end of the tubing 130 is arranged on a side surface of the housing 105 and, due to serval bends, guided along the periphery of the recess area 106 inside the recess area 106. The tubing 130 is thereby forming a closed loop around the plurality of feedthrough conductors 110 so that an axial end surface of the tubing 130 abuts against the outer peripheral surface of said tubing 130. Alternatively, the tubing 130 may be guided along only a part of the recess area 106 without the axial end face of the tubing 130 abutting against the outer peripheral surface of said tubing 130.

The end of the tubing 130 arranged on the housing 105 has a longitudinal slit 140 cut through the wall of the tubing 130. The longitudinal slit 140 extends from the axial end surface of the tubing 130 along the closed loop around the feedthrough conductors 110.

Further, a set of twenty-one substantially perpendicular slits 150 are cut through the wall of the tubing 130. Each of the twenty-one slits 150 intersects with the longitudinal slit 140 in a substantially perpendicular angle. Each of the twenty-one substantially perpendicular slits 150 is placed in proximity to a respective feedthrough conductor 110. Thereby, each of the substantially perpendicular slits 150 is formed at a different longitudinal position of the tubing 130.

At the inside of the tubing 130, a plurality of electrical wires 125 is housed. At the one end of the tubing 130 extending from the housing 105, twenty-one wires 125 are running jointly inside the tubing 130 towards the electrodes of the implantable medical device 100, while maintained electrically insulated. At the other end of the tubing 130 arranged on the housing 105, one wire 125 is passed through each of the substantially perpendicular slits 150 in order to extend from the tubing 130 towards a respective feedthrough conductor 110, to which it is to be connected.

The implantable medical device 100 further comprises a wire guide 160 arranged on a side surface of the housing 105. The wire guide 160 is made of an electrically non-conductive material in order to provide electrical insulation for the surrounding members.

The wire guide 160 is arranged in the recess area 106 of the side surface of the housing 105 and the shape of the wire guide 160 corresponds to the shape of the recess area 106. A height of the wire guide 160 corresponds to a depth of the recess area 106 so that the upper surface of the wire guide 160 is substantially flush with the surrounding part of the side surface of the housing 105. The wire guide 160 has a plurality of through holes 170 formed at positions corresponding to the arrangement of the feedthrough conductors 110. Thereby, each feedthrough conductor 110 is exposed through a separate through hole 170 of the wire guide 160. The surrounding part of the protrusion area 107 inside the recess area 106 is covered by the wire guide 160.

Further, the wire guide 160 is arranged inside the loop formed by the tubing 130 so that the tubing 130 abuts against an outer periphery of the wire guide 160.

A plurality of guide grooves 165 are formed in the wire guide 160 in order to guide the electrical wires 125 extending from the tubing 130. The number of guide grooves 165 corresponds to the number of wires 125 in order to guide each wire 125 electrically insulated in a separate guide groove 165.

Each guide groove 165 is open towards the same side of the wire guide 160.

A first end of each guide groove 165 is arranged close or communicates with a respective substantially perpendicular slit 150 of the tubing 130 through which a wire 125 is passed. A second end of each guide groove 165 communicates with a through hole 170 through which a respective feedthrough conductor 110 is exposed. Thereby, each wire 125 is guided in the wire guide 160 from the wire 125 exit position at the tubing 130 to the feedthrough conductor 110, to which it is to be connected.

A plurality of spatially separated connectors 120 are configured to provide terminal connections for the plurality of electrical wires 125. Each connector 120 serves as a link between a wire 125 and a feedthrough conductor 110, thereby providing an electrical connection. The connectors 120 are attached to the wires 125 by electrical welding. The connection between the connectors 120 and the feedthrough conductors 110 is made by laser welding. Alternatively, the connections may be made by other joining methods such as soldering, clamping, screwing, or riveting.

A final overmolding (not shown) is applied to cover the housing 105, the tubing 130, the wire guide 160 and the connections between the wires 125 and the feedthrough conductors 110.

A method of providing wire connections for the implantable medical device 100 will be described below.

A sealed flat housing 105 enclosing an electronic circuitry and a plurality of feedthrough conductors 110 is prepared. A wire guide 160 is placed on a side surface of the housing 105 so that a distal end part of each feedthrough conductor 110 is exposed.

A tubing 130 housing a plurality of wires 125 is taken and a longitudinal slit 140 is cut through the wall of the tubing 130. Twenty-one slits 150 are cut through the wall of the tubing 130 at different longitudinal positions and each slit 150 substantially perpendicular to the longitudinal slit 140. Each of the wires 125 is then pulled through the longitudinal slit 140 to the outside of the tubing 130, starting at the end of the tubing 130 distal from the electrodes of the implantable medical device 100. When pulling along the longitudinal slit 140, each wire 125 is passed through an individual substantially perpendicular slit 150 of the tubing 130 so as to fix the longitudinal position from where the wire 125 extends. Next, the wires 125 are cut at the same extension length from the tubing 130. Twenty-one connectors 120 are connected to the twenty-one free wire 125 ends by electrical welding.

The tubing 130 is arranged on the housing 105 around the wire guide 160 with the wires 125 extending inward to the wire guide 160. Each wire 125 is guided inside a separate guide groove 165 from the wire 125 exit position at the tubing 130 to a feedthrough conductor 110. The connectors 120 on the free ends of the wires 125 are then connected to the distal end parts of the feedthrough conductors 110 by laser welding. A final overmolding is applied to cover the housing 105, the tubing 130, the wire guide 160 and the connections between the wires 125 and the feedthrough conductors 110.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. An implantable medical device comprising
a sealed flat housing enclosing an electronic circuitry;
a plurality of feedthrough conductors, each feedthrough conductor comprising a proximal end part connected to the enclosed electronic circuitry and a distal end part extending from a side surface of the housing and cumulated on said side surface;
a tubing that houses a plurality of wires connected to said feedthrough conductors and that is arranged on the housing; and
a longitudinal slit through the wall of the tubing through which the wires extend out of the tubing; wherein the tubing has at least one slit substantially perpendicular to the longitudinal slit and at least one wire exits the tubing through one of the slits.

2. The implantable medical device according to claim 1, wherein at least two wires extend out of the tubing at different longitudinal positions of the tubing.

3. The implantable medical device according claim 2, wherein a wire length from a wire exit position at the tubing to a fixed wire end is the same for the at least two wires.

4. The implantable medical device according to claim 2, wherein wire extension directions from wire exit positions at the tubing to fixed wire ends are different for the at least two wires.

5. The implantable medical device according claim 1, wherein a wire length from a wire exit position at the tubing to a fixed wire end is the same for the at least two wires.

6. The implantable medical device according to claim 1, wherein wire extension directions from wire exit positions at the tubing to fixed wire ends are different for the at least two wires.

7. The implantable medical device according to claim 1, further comprising a wire guide arranged on said side surface in which a plurality of guide grooves for guiding the wires are formed.

8. The implantable medical device according to claim 7, wherein the tubing runs along the outer periphery of the wire guide.

9. The implantable medical device according to claim 7, wherein the wire guide has a hole through which the distal end part of the feedthrough conductor is exposed.

10. The implantable medical device according to claim 7, wherein a first end of each guide groove communicates with an outer periphery of the wire guide and a second end of each guide groove communicates with the feedthrough conductor.

11. The implantable medical device according to claim 7, wherein the wire guide is made from an electrically insulating material to house the wires electrically insulated from each other and from the housing.

12. The implantable medical device according to claim 1, further comprising a plurality of connectors configured to provide connections for the plurality of wires, wherein each connector comprises a first end section adapted to be connected with a feedthrough conductor and a second end section adapted to be connected with a wire.

13. A method of providing connections for a plurality of wires in an implantable medical device, the method comprising
preparing a sealed flat housing enclosing an electronic circuitry, said housing comprising a plurality of feedthrough conductors, each feedthrough conductor comprising a proximal end part connected to the enclosed electronic circuitry and a distal end part extending from a side surface of the housing and cumulated on said side surface;
cutting a longitudinal slit through the wall of a tubing and passing wires through the slit;
arranging the tubing on said housing and connecting each wire to a corresponding feedthrough conductor; and
cutting at least one slit substantially perpendicular to the longitudinal slit and passing at least one wire through one of the slits.

14. The method according to claim 13, further comprising passing at least two wires through the slit at different longitudinal positions of the tubing and cutting the wires so that a wire length from a wire exit position at the tubing to a wire end is the same for the at least two wires.

15. The method according to claim 13, further comprising arranging a wire guide, in which a plurality of guide grooves for guiding the wires are formed, on a side surface of the housing and placing the wires in the guide grooves.

* * * * *